(12) United States Patent
Vitt et al.

(10) Patent No.: US 10,209,123 B2
(45) Date of Patent: Feb. 19, 2019

(54) LIQUID DETECTION FOR AN ACOUSTIC MODULE

(71) Applicant: Apple Inc., Cupertino, CA (US)

(72) Inventors: Nikolas T. Vitt, Cupertino, CA (US); Ruchir M Dave, Cupertino, CA (US); Jesse A. Lippert, Cupertino, CA (US); Brad G. Boozer, Cupertino, CA (US); Neal D. Evans, Cupertino, CA (US); David S. Wilkes, Jr., Cupertino, CA (US)

(73) Assignee: Apple Inc., Cupertino, CA (US)

( * ) Notice: Subject to any disclaimer, the term of this patent is extended or adjusted under 35 U.S.C. 154(b) by 252 days.

(21) Appl. No.: 15/245,856

(22) Filed: Aug. 24, 2016

(65) Prior Publication Data

US 2018/0058918 A1  Mar. 1, 2018

(51) Int. Cl.
*G01H 15/00* (2006.01)
*G01N 29/028* (2006.01)
*G01H 13/00* (2006.01)

(52) U.S. Cl.
CPC ............. *G01H 15/00* (2013.01); *G01H 13/00* (2013.01); *G01N 29/028* (2013.01)

(58) Field of Classification Search
CPC ....... G01H 15/00; G01H 13/00; G01N 29/028
USPC .......................................... 73/574, 587, 579
See application file for complete search history.

(56) References Cited

U.S. PATENT DOCUMENTS

| 3,987,258 A | 10/1976 | Tsutsui |
| 4,868,799 A | 9/1989 | Massa |
| 5,117,403 A | 5/1992 | Eberl et al. |
| 5,349,140 A | 9/1994 | Valenzin |
| 5,812,496 A | 9/1998 | Peck |

(Continued)

FOREIGN PATENT DOCUMENTS

| CN | 1642355 | 7/2005 |
| CN | 1933679 | 3/2007 |

(Continued)

OTHER PUBLICATIONS

Consumerist, "Cellphone Battery Designed to Fail at First Drop of Water?" Consumerist, Sep. 22, 2007 (Sep. 22, 2007), XP055199652, Retrieved from the Internet: URL:http://consumerist.com/2007/09/22/cellphone-battery-designed-to-fail-at-first-drop-of-water/ [retrieved on Jul. 2, 2015], 4 pages.

(Continued)

*Primary Examiner* — Justin Seo
*Assistant Examiner* — Rose M Miller
(74) *Attorney, Agent, or Firm* — Brownstein Hyatt Farber Schreck, LLP

(57) ABSTRACT

An acoustic module is coupled to an acoustic passage. The acoustic module includes an acoustic transducer coupled to a diaphragm. A controller or other circuitry measures an impedance of the acoustic transducer. Based on the impedance, the controller determines whether the impedance indicates that the acoustic passage is blocked. The controller may determine that the acoustic passage is blocked by liquid that is present in the acoustic passage. When the controller determines based on the impedance that liquid is present in the acoustic passage, the controller may drive out, purge, and/or otherwise remove the liquid, such as by using the acoustic transducer to vibrate the diaphragm.

20 Claims, 13 Drawing Sheets

(56) References Cited

U.S. PATENT DOCUMENTS

| | | | |
|---|---|---|---|
| 6,007,105 A | 12/1999 | Dietle et al. | |
| 6,064,909 A | 5/2000 | Barkley et al. | |
| 6,128,394 A | 10/2000 | Hayakawa | |
| 6,486,398 B1 | 11/2002 | McCulloch | |
| 6,785,395 B1 | 8/2004 | Ameson | |
| 6,899,794 B1 | 5/2005 | Yamada | |
| 6,932,187 B2 | 8/2005 | Banter et al. | |
| 7,245,733 B2 | 7/2007 | Saltykov | |
| 7,480,209 B2 | 1/2009 | Giles | |
| 7,499,561 B2 | 3/2009 | Hanses et al. | |
| 7,577,345 B2 | 8/2009 | Tei et al. | |
| 7,707,877 B2 | 5/2010 | Nishizu et al. | |
| 7,876,919 B2 | 1/2011 | Ram et al. | |
| 7,894,621 B2 | 2/2011 | Jensen | |
| 7,991,173 B2 | 8/2011 | Ueki | |
| 8,055,003 B2 | 11/2011 | Mittleman et al. | |
| 8,059,490 B2 | 11/2011 | Rapps et al. | |
| 8,112,130 B2 | 2/2012 | Mittleman et al. | |
| 8,135,149 B2 | 3/2012 | Yoshida et al. | |
| 8,157,048 B2 | 4/2012 | Banter et al. | |
| 8,170,266 B2 | 5/2012 | Hopkinson et al. | |
| 8,175,321 B2 | 5/2012 | Bryant et al. | |
| 8,185,166 B2 | 5/2012 | Weber et al. | |
| 8,220,142 B2 | 7/2012 | Lim | |
| 8,229,153 B2 | 7/2012 | Mittleman et al. | |
| 8,233,646 B2 | 7/2012 | Lutz | |
| 8,272,517 B2 | 9/2012 | Horie et al. | |
| 8,416,089 B1 | 4/2013 | Clary | |
| 8,638,970 B2 | 1/2014 | Burton | |
| 8,644,530 B2 | 2/2014 | Soininen et al. | |
| 8,670,586 B1 | 3/2014 | Boyle et al. | |
| 8,687,828 B2 | 4/2014 | Otani et al. | |
| 8,724,841 B2 | 5/2014 | Bright et al. | |
| 8,792,665 B2 | 7/2014 | Lin | |
| 8,803,745 B2 | 8/2014 | Dabov | |
| 8,811,634 B2 | 8/2014 | Kaplan et al. | |
| 8,883,289 B2 | 11/2014 | Tsao et al. | |
| 8,923,528 B2 | 12/2014 | Arche | |
| 8,939,252 B2 | 1/2015 | Sanborn | |
| 8,942,401 B2 | 1/2015 | Murayama | |
| 8,965,030 B2 | 2/2015 | Aase | |
| 8,986,802 B2 | 3/2015 | Karube et al. | |
| 9,038,773 B2 | 5/2015 | Banter | |
| 9,078,063 B2 | 7/2015 | Loeppert et al. | |
| 9,132,270 B2 | 9/2015 | Vaishya | |
| 9,171,535 B2 | 10/2015 | Abe et al. | |
| 9,226,076 B2 | 12/2015 | Lippert et al. | |
| 9,253,297 B2 | 2/2016 | Abe et al. | |
| 9,317,068 B2 | 4/2016 | Sanders | |
| 9,363,589 B2 | 6/2016 | Lippert et al. | |
| 9,414,141 B2 | 8/2016 | Cohen et al. | |
| 9,681,210 B1 | 6/2017 | Lippert et al. | |
| 2002/0015068 A1* | 2/2002 | Tsukada | B41J 29/38 347/19 |
| 2002/0170353 A1* | 11/2002 | Usui | B41J 2/17503 73/290 V |
| 2004/0029530 A1 | 2/2004 | Noguchi et al. | |
| 2005/0134473 A1 | 6/2005 | Jang et al. | |
| 2006/0045301 A1 | 3/2006 | Jakubaitis | |
| 2006/0198547 A1 | 9/2006 | Hampton | |
| 2007/0003081 A1 | 1/2007 | Ram et al. | |
| 2007/0035865 A1 | 2/2007 | Chashi | |
| 2007/0113964 A1 | 4/2007 | Crawford et al. | |
| 2007/0263878 A1 | 11/2007 | Yu | |
| 2008/0149417 A1 | 6/2008 | Dinh | |
| 2009/0230487 A1 | 9/2009 | Saitoh et al. | |
| 2010/0098261 A1* | 4/2010 | Norhammar | H04M 1/6066 381/59 |
| 2011/0013799 A1 | 1/2011 | Fang et al. | |
| 2011/0298184 A1 | 12/2011 | Aurelius | |
| 2011/0317868 A1 | 12/2011 | Tsujii | |
| 2012/0177239 A1 | 7/2012 | Lee | |
| 2012/0195455 A1 | 8/2012 | Chiba et al. | |
| 2013/0287213 A1 | 10/2013 | Sekiyama | |
| 2013/0296994 A1 | 11/2013 | Vaishya | |
| 2013/0335211 A1 | 12/2013 | Kobayashi | |
| 2014/0044297 A1 | 2/2014 | Loeppert et al. | |
| 2014/0064546 A1 | 3/2014 | Szczech | |
| 2014/0093095 A1 | 4/2014 | Slotte et al. | |
| 2014/0219646 A1 | 8/2014 | Hooton et al. | |
| 2014/0254849 A1 | 9/2014 | Abe et al. | |
| 2014/0369547 A1 | 12/2014 | Qingshan | |
| 2015/0016648 A1 | 1/2015 | Kazemzadeh et al. | |
| 2015/0029112 A1* | 1/2015 | Macours | H03K 17/96 345/173 |
| 2015/0030167 A1* | 1/2015 | Pan | H04R 3/007 381/59 |
| 2015/0030169 A1* | 1/2015 | Pan | H05K 999/99 381/59 |
| 2015/0146905 A1 | 5/2015 | Abe et al. | |
| 2015/0163572 A1 | 6/2015 | Weiss et al. | |
| 2015/0237431 A1 | 8/2015 | Jeziorek et al. | |
| 2015/0304767 A1 | 10/2015 | Mori | |
| 2016/0205469 A1 | 7/2016 | Steijner et al. | |
| 2016/0212526 A1 | 7/2016 | Salvatti et al. | |
| 2017/0041712 A1 | 2/2017 | Lippert et al. | |
| 2017/0227498 A1* | 8/2017 | Miller | G01N 29/04 |
| 2017/0227499 A1* | 8/2017 | Miller | G01N 29/04 |
| 2017/0371616 A1* | 12/2017 | Su | G06F 3/165 |

FOREIGN PATENT DOCUMENTS

| | | | |
|---|---|---|---|
| CN | 201210732 | 3/2009 | |
| CN | 101467468 | 6/2009 | |
| EP | 1079664 | 2/2001 | |
| EP | 1998591 | 12/2008 | |
| JP | WO 2004043113 A1 * | 5/2004 | H04R 9/10 |
| JP | 2004312156 | 11/2004 | |
| JP | 2011188191 | 9/2011 | |
| JP | WO 2011125804 A1 * | 10/2011 | H04R 9/06 |
| JP | 2013115549 | 6/2013 | |
| WO | WO 15/047378 | 4/2015 | |

OTHER PUBLICATIONS

The Gadget Show, "What to do when gadgets get wet," Retrieved from the Internet: URL:http://gadgetshow.channel5.com/gadget-show/blog/what-to-do-when-gadgets-get-wet [retrieved on Apr. 9, 2014], p. 2, paragraph 1, 2 pages.

Nakano et al., "Helmholtz resonance technique for measuring liquid volumes under micro-gravity conditions," *Microgravity Sci. Technol.*, XVII-3, 2005, pp. 64-70.

* cited by examiner

LIQUID DETECTION FOR AN ACOUSTIC MODULE

FIELD

The described embodiments relate generally to acoustic modules, such as speakers and microphones. More particularly, the present embodiments relate to detection of liquid in an acoustic module by measuring a change in impedance or response of an acoustic transducer.

BACKGROUND

Many electronic devices include acoustic devices (such as microphones or speakers) in order to record sound, output sound, and/or perform other functions. In order to transmit sound, an acoustic device may be coupled to an external environment through an acoustic path. However, the acoustic path may expose the acoustic device to liquids or other contaminants from the external environment. The presence of liquid or other contaminants on or around the acoustic device may adversely affect the performance of the device. The present disclosure is directed to systems and techniques for detecting and/or removing a liquid or other contaminant from an acoustic device.

SUMMARY

The present disclosure relates to detection of liquid in an acoustic module using impedance. Blockages in an acoustic passage faced by an acoustic module alter the impedance of an acoustic transducer coupled to a diaphragm of the acoustic module. The acoustic module and/or an associated electronic device measures the impedance to determine whether or not a blockage is present. In various implementations, the liquid may also be removed, such as by producing tones, noise, or other sound waves to drive out the liquid.

In some embodiments, an electronic device includes a housing, an acoustic passage internal to the housing, an acoustic transducer coupled to the acoustic passage, and circuitry electrically coupled to the acoustic transducer. The circuitry is operable to measure an impedance of the acoustic transducer at approximately a reference frequency of the acoustic transducer and detect a presence of liquid based on the measured impedance.

In various examples, the reference frequency corresponds to a resonant frequency of the acoustic transducer in an unobstructed condition. In some implementations, the presence of liquid is detected based on a reduction of impedance over a range of frequencies that includes the resonant frequency as compared to a reference value and the reference value corresponds to an operation of the acoustic transducer without the presence of liquid. In various implementations, the presence of liquid is detected when the measured impedance is approximately equal to the impedance of the acoustic transducer when dry at a non-resonant frequency.

In numerous examples, the circuitry is further operable to apply a drive signal to a transducer, the drive signal is configured to purge the liquid from the acoustic passage. In various implementations, the transducer is the acoustic transducer and the drive signal is a voltage signal. In some implementations, the transducer is separate from the acoustic transducer. In numerous examples, the circuitry is further operable to measure an updated impedance of the acoustic transducer while applying the drive signal and adjust the drive signal based on the updated impedance.

In various embodiments, an electronic device includes a housing; a port defined in the housing; an acoustic module coupled to the port, the acoustic module including an acoustic transducer; and a controller coupled to the acoustic module. The controller is operable to measure an impedance of the acoustic transducer at approximately a resonant frequency of the acoustic transducer and determine a blockage condition based on the measured impedance.

In some examples, the controller is further operable to distinguish if the blockage condition is due to a blockage of the port or a foreign material within the housing. In various implementations, the controller is further configured to estimate a type of foreign material within the housing based on the measured impedance.

In various examples, the controller measures the impedance prior to signaling the acoustic module to provide output. In some examples, the acoustic module comprises at least one of a speaker or a microphone.

In numerous examples, the electronic device further comprises a microphone coupled to the controller. In some implementations of such examples, the controller is further configured to measure an ambient acoustic level and, in response to the measured ambient acoustic level exceeding a threshold, drive the acoustic transducer at the resonant frequency and measure the impedance of the acoustic transducer.

In numerous embodiments, an electronic device includes an enclosure; an acoustic module including an acoustic transducer, the acoustic module coupled to a passage within an interior of the enclosure; a detector coupled to the acoustic transducer operable to measure a change in impedance of the acoustic transducer; and a processing unit coupled to the detector. The processing unit is operable to determine a blockage condition based on the change in impedance.

In some examples, the detector comprises a sensing resistor. In various examples, the processing unit uses the impedance to determine at least one of an amount of a contaminant or a type of a contaminant. In numerous examples, the electronic device further includes a capacitive touch component coupled to the processing unit and the detector measures the impedance in response to a signal from the capacitive touch component. In various examples, the processing unit is operable to respond to a query regarding whether the electronic device has been exposed to contaminants. In some examples, the processing unit is operable to prompt a user before attempting to remove contaminants from the passage.

BRIEF DESCRIPTION OF THE DRAWINGS

The disclosure will be readily understood by the following detailed description in conjunction with the accompanying drawings, wherein like reference numerals designate like structural elements.

DETAILED DESCRIPTION

Figure 1:
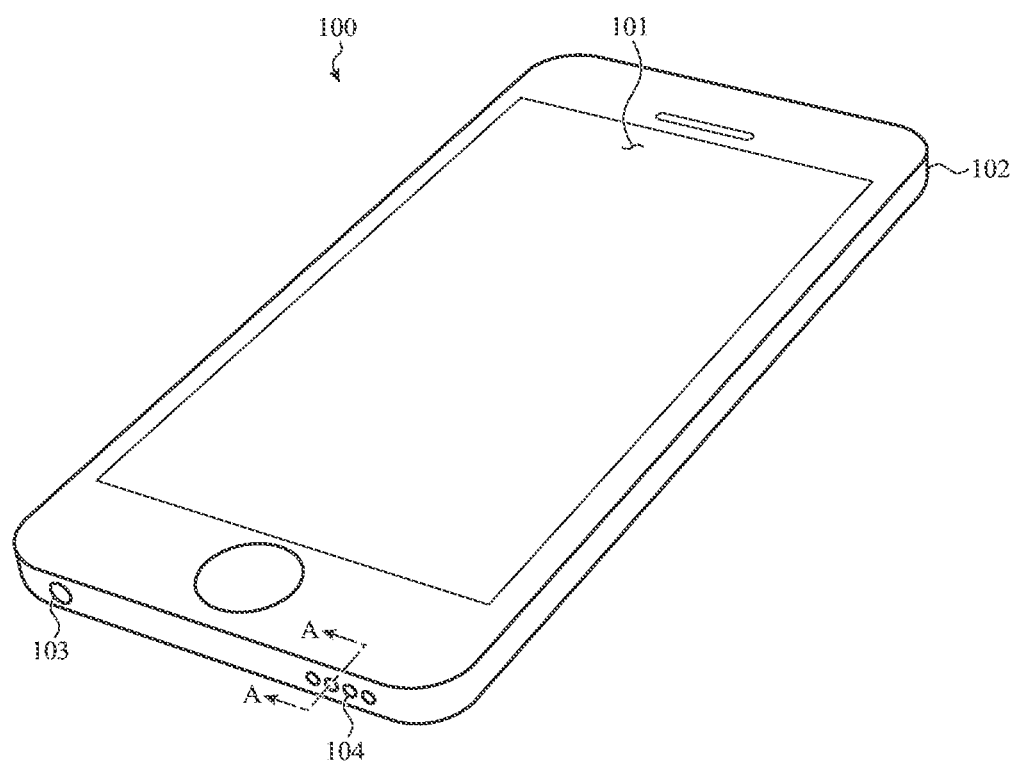
FIG. 1 depicts an electronic device having an acoustic module.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The description that follows includes sample systems, methods, and apparatuses that embody various elements of the present disclosure. However, it should be understood that the described disclosure may be practiced in a variety of forms in addition to those described herein.

The following disclosure relates to detection of liquid in an acoustic module. For purposes of the following disclosure, an acoustic module may refer to a speaker, microphone, or other device configured to transmit or receive acoustic energy. The presence of liquid may be detected by measuring a change in impedance or an impedance profile over a range of frequencies. In some cases, the acoustic module includes an acoustic transducer or voice coil that is coupled to a diaphragm. The diaphragm may be coupled or otherwise in communication with an acoustic passage through which sound waves produced or received by the diaphragm travel. Blockages in the acoustic passage (such as liquid in the passage contacting the diaphragm, a finger covering an acoustic opening connecting the acoustic passage to an external environment, and so on) may alter the impedance of the acoustic transducer. By measuring and evaluating the impedance and/or a change in impedance, the presence of a blockage or ingress of a liquid or other contaminant may be detected.

In some embodiments, a determination may be made as to the type of obstruction that may be present. For example, by analyzing the impedance or change in impedance, a determination may be made as to whether the acoustic device is blocked or that a liquid or other contaminant is present within or on a diaphragm of the acoustic module. By way of example, by analyzing the impedance, the acoustic module and/or the associated electronic device may determine whether the obstruction is due to liquid, dirt, and/or other contaminants present in the acoustic passage, whether the acoustic opening connecting the acoustic passage and an external environment is covered, the amount and/or type of contaminant present in the acoustic passage, and so on.

In some implementations, in response to detecting a blockage of a particular type, the acoustic module and/or the associated electronic device may drive out, purge, and/or otherwise remove the blockage. For example, when the blockage is a liquid present in the acoustic passage, the diaphragm may be driven with a specially configured tone or response to drive the liquid out of the device. In some cases, a separate transducer is used to alleviate the blockage.

In various implementations, the acoustic module and/or an associated electronic device may minimize a user perceptibility of the blockage detection and/or removal. For example, where detection and/or removal produces sound, the detection and/or removal may be delayed until an ambient or other sound level is above a threshold so that the produced sound is less perceptible. In some cases, the detection and/or removal may be delayed until the user responds to a prompt or other cue to avoid an undesired or unexpected acoustic output.

The impedance of the acoustic transducer may be monitored in different manners in different implementations. The impedance may be monitored continuously, periodically, upon the occurrence of a triggering event, and so on. For example, in various implementations, the impedance may be measured once per hour, at a user specified interval, prior to using the acoustic module to provide output, upon receiving a signal from another sensor or device, and so on.

These and other embodiments are discussed below with reference to FIGS. 1-9. However, those skilled in the art will readily appreciate that the detailed description given herein with respect to these Figures is for explanatory purposes only and should not be construed as limiting.

FIG. 1 depicts an electronic device 100 having an acoustic module. In accordance with some embodiments, the electronic device 100 is configured to detect liquid or other foreign material or contaminant in an acoustic module using a measured impedance or change in impedance. In this example, the electronic device 100 is depicted as a smart phone having a touch sensor 101 or touch screen that is configured to receive touch input from a user. The electronic device 100 also includes a housing 102 or other enclosure that defines an exterior surface of the electronic device 100 and an internal volume that houses the internal components of the electronic device 100. In this example, the housing 102 includes multiple openings for various acoustic devices. Specifically, the housing 102 defines an acoustic opening 103 for a microphone or other acoustic device and a set of acoustic openings 104 for a speaker or other acoustic device.

While the present example is provided with respect to a smart phone, the embodiments described herein may also be applied to a variety of electronic devices including, for example, a wearable electronic device, a notebook computing device, a tablet computing device, a portable media player, a health monitoring device, and other portable electronic devices that include a speaker or other acoustic module. The embodiments described herein may also be applied to a desktop computing device, an electronic appliance, display device, external microphone or speaker, printer, keyboard device, or other electronic device having an acoustic module.

The electronic device 100 is operable to determine whether or not liquid (or other foreign contaminant) is present in an acoustic passage or port connected to the set of acoustic openings 104 based on a measured impedance or change in impedance of the acoustic transducer. If liquid is detected, the electronic device 100 may perform one or more actions to drive out, purge, and/or otherwise remove the liquid from the acoustic passage. The electronic device 100 may also be configured to distinguish between a blockage of one of the acoustic openings 103, 104 and a foreign contaminant present within the housing 102 of the electronic device 100.

Figure 2A:
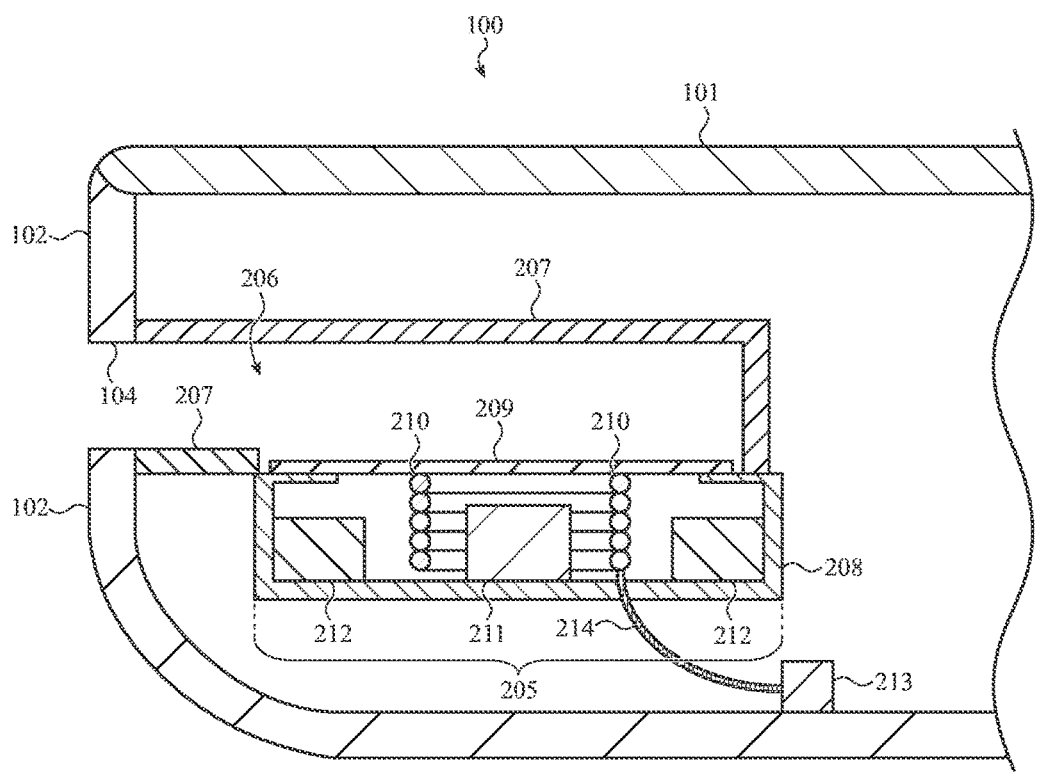
FIG. 2A depicts a cross-sectional view of an example of the electronic device of FIG. 1, taken along line A-A of FIG. 1.

FIG. 2A depicts a cross-sectional view of an example of the electronic device 100 of FIG. 1, taken along line A-A of FIG. 1. The example acoustic module 205 may be coupled to control circuitry 213 that is configured to detect a blockage based on an impedance measurement. In some embodiments, the control circuitry 213 is configured to measure the impedance or a change in impedance at or around a reference frequency of the acoustic module 205. The reference frequency may correspond to the resonance frequency of the acoustic module 205 when dry or un-obstructed.

As shown in FIG. 2A, the acoustic module 205 is disposed within an internal volume or interior defined within the housing 102. A structure 207 (or housing, enclosure, and so on) may include a wall or other structural element that is coupled to the housing 102 and defines the acoustic passage 206 or channel between the acoustic module 205 and one or more of the set of acoustic openings 104. The acoustic passage 206 allows acoustic energy (e.g., sound waves, acoustic signals) to be transmitted between the acoustic module 205 and the external environment via the acoustic opening 104.

As shown in FIG. 2A, the acoustic module 205 includes an acoustic transducer having a diaphragm 209 coupled to an enclosure 208 and a voice coil 210 coupled to the diaphragm 209. A center magnet 211 and a side magnet 212 may also be coupled to the enclosure 208. If operating as a speaker, the voice coil 210 is configured to electromagnetically couple to the magnets 211, 212 and displace the diaphragm 209 to produce an acoustic signal. If operating as a microphone, acoustic energy may cause the diaphragm 209 to displace, which causes a movement of the voice coil 210 with respect to the magnets 211, 212 and results in an electrical signal (e.g., a current signal) being generated by the voice coil 210.

In the example of FIG. 2A, the device includes control circuitry 213 that is operatively coupled to the acoustic module 205. In some instances, the control circuitry 213 includes a processing unit, controller, or other control circuitry that is configured to control or interface with the acoustic module 205. The control circuitry 213 may also include a driver and/or sensing circuitry that is configured to send and/or receive electrical signals to or from the voice coil 210 via an electrical connection 214. If operating as a speaker, the control circuitry 213 may be configured to deliver a current signal to drive the voice coil 210 and produce an acoustic signal. In some cases, the voice coil 210 generates a magnetic flux when an alternating current passes through the voice coil 210. This magnetic flux interacts with magnetic fields of the center magnet 211 and side magnets 212 to vibrate and/or otherwise displace the diaphragm 209 and produce sound waves or other acoustic energy.

In this example, the acoustic module 205 is a speaker. However, it is understood that this is an example. In various implementations, the acoustic module 205 may be any kind of acoustic device, such as a microphone, that includes a voice coil 210 and a diaphragm 209. If operating as a microphone, the control circuitry 213 may be configured to detect a current signal produced by the voice coil 210, which may correspond to an acoustic signal received by the acoustic module 205.

Optimal operation of the acoustic module 205 may depend on free movement of the diaphragm 209 and the ability of sound waves or acoustic energy to travel through the acoustic passage 206 unimpeded. In the example of a speaker, sound waves generated by movement of the diaphragm 209 may travel through the acoustic passage 206 out one or more of the set of acoustic openings 104. In the example of a microphone, sound waves may travel in one or more of the set of acoustic openings 104, travel through the acoustic passage 206, and vibrate or otherwise move the diaphragm 209, generating current through the voice coil 210. Regardless, a partial or full blockage of the passage may inhibit sound waves from travelling (and/or impair the travel of the sound waves) through the acoustic passage 206 and/or one or more of the set of acoustic openings 104. A partial and/or full blockage may also restrict or impair motion of the diaphragm 209, which may alter or impair performance of the acoustic module 205.

Figure 2B:
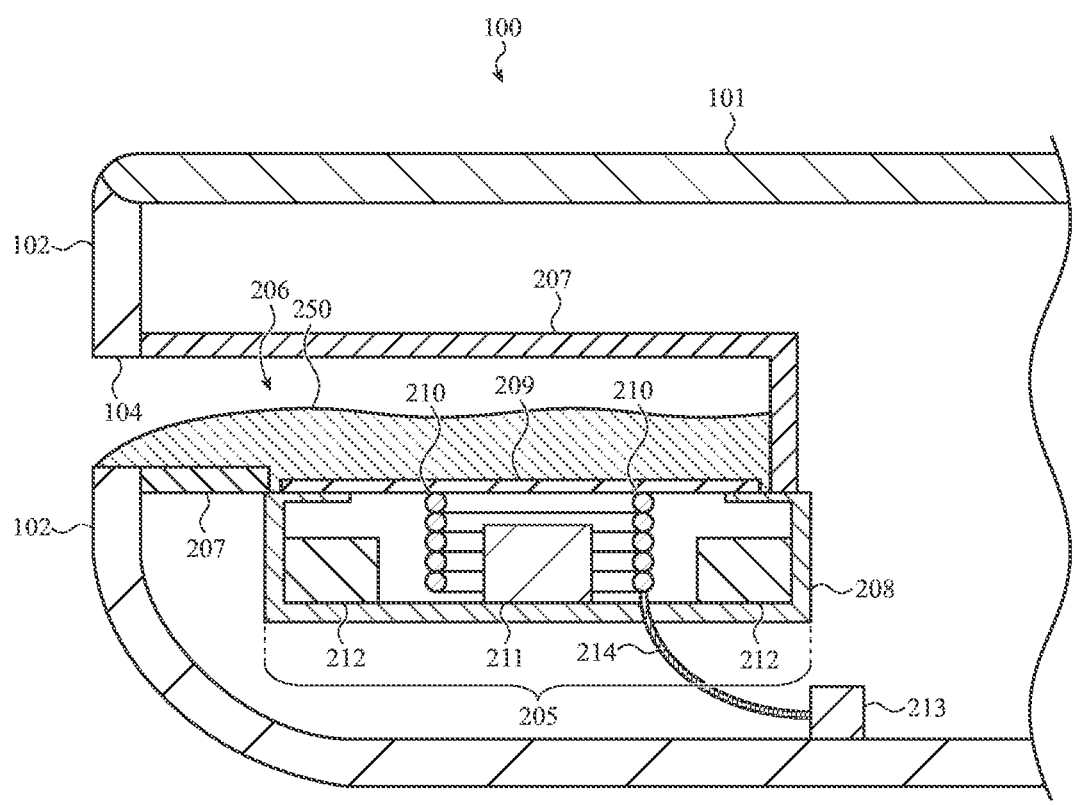
FIG. 2B depicts the electronic device of FIG. 2A with liquid present in the acoustic passage.

FIG. 2B depicts an example of an acoustic module 205 having a first type of blockage. In particular, the acoustic module 205 includes a foreign object 250 (e.g., a liquid) present in the acoustic passage 206. This type of blockage may have two primary effects: the liquid may restrict motion of the diaphragm 209 and/or may impair movement of sound waves through the acoustic passage 206. This may distort or reduce sound produced by the acoustic module 205, prevent the acoustic module 205 from generating sound, distort or reduce sound detected by the acoustic module 205, prevent the acoustic module 205 from detecting sound, and so on.

Figure 2C:
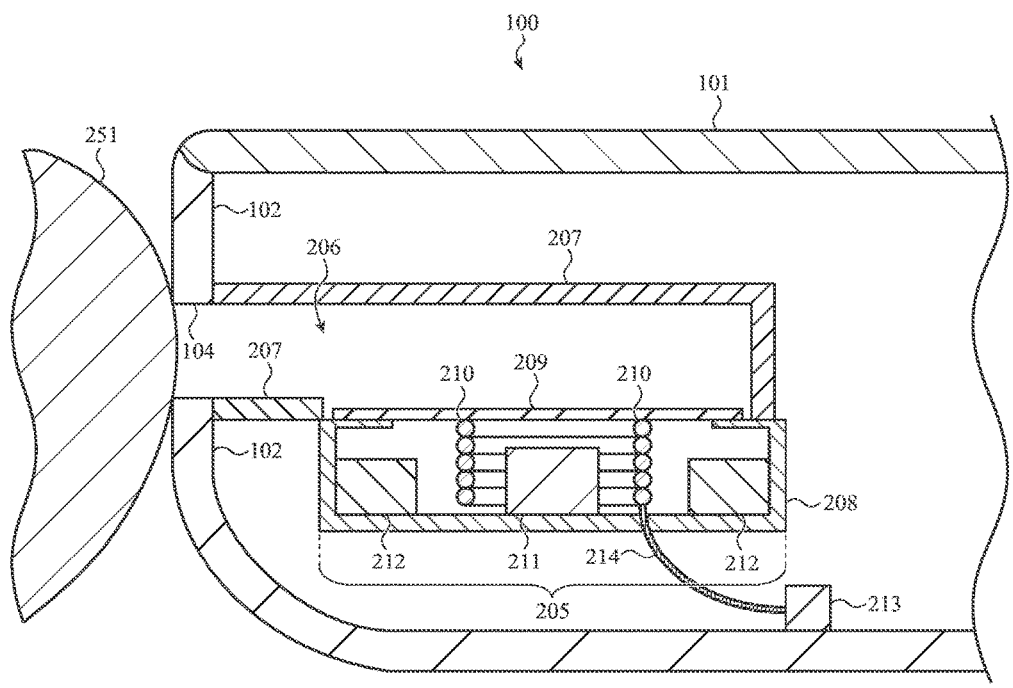
FIG. 2C depicts the electronic device of FIG. 2A with an object covering the acoustic opening.

FIG. 2C depicts another example of an acoustic module 205 having a second type of blockage. In particular, the acoustic module 205 includes an object 251 (e.g., a finger) blocking one or more of the set of acoustic openings 104. This type of blockage may impair movement of sound waves through the acoustic passage 206 and/or may dampen the sound that is produced or received by the acoustic module 205.

In some cases, blocking the one or more of the set of acoustic openings 104 may also restrict motion of the diaphragm 209 due to air pressure in the acoustic passage 206. However, as the object 251 does not directly contact the diaphragm 209, any restriction to the movement of the diaphragm 209 motion would be different than the blockage due to the foreign object 250 illustrated in FIG. 2B.

With regard to the example embodiments of FIGS. 2B-2C, a partial or full blockage of the acoustic passage 206 may alter or affect the impedance of the voice coil 210 as compared to normal or dry operating conditions depicted in FIG. 2A. As described in more detail below, by analyzing the impedance of the voice coil 210, the control circuitry 213 may determine whether a blockage is present and/or the type of blockage that has likely occurred. This information may be used to initiate an evacuation measure or procedure.

Figure 3A:
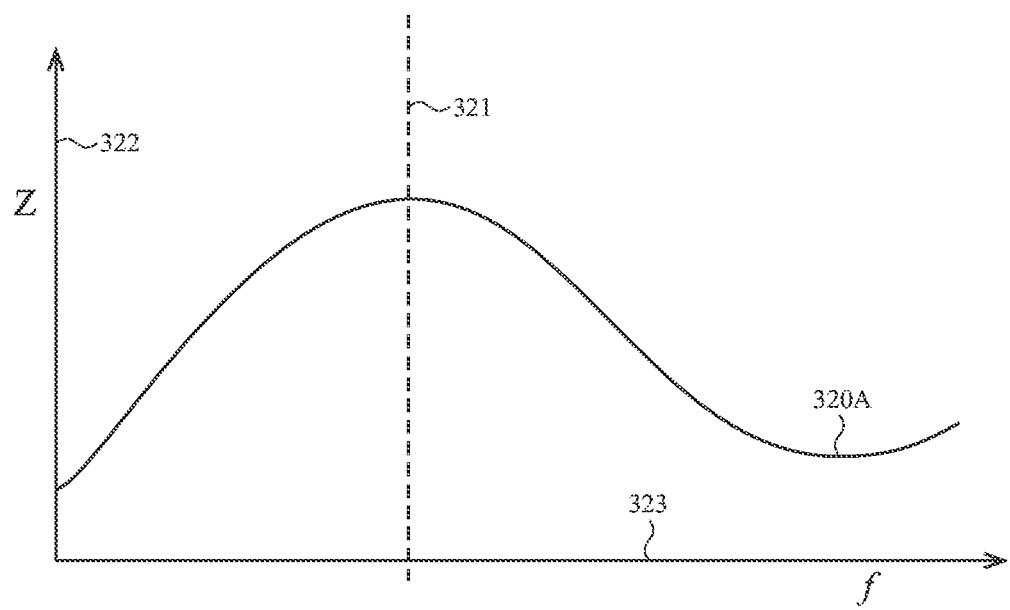
FIG. 3A depicts an example impedance curve of the acoustic transducer of FIG. 2A.
Figure 3B:
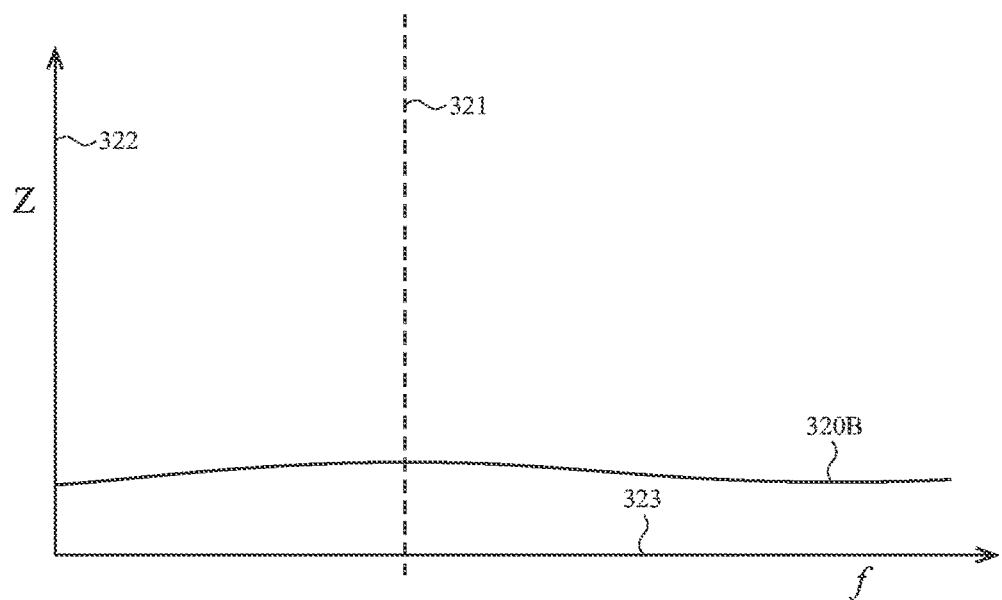
FIG. 3B depicts another example impedance curve of the acoustic transducer of FIG. 2B.
Figure 3C:
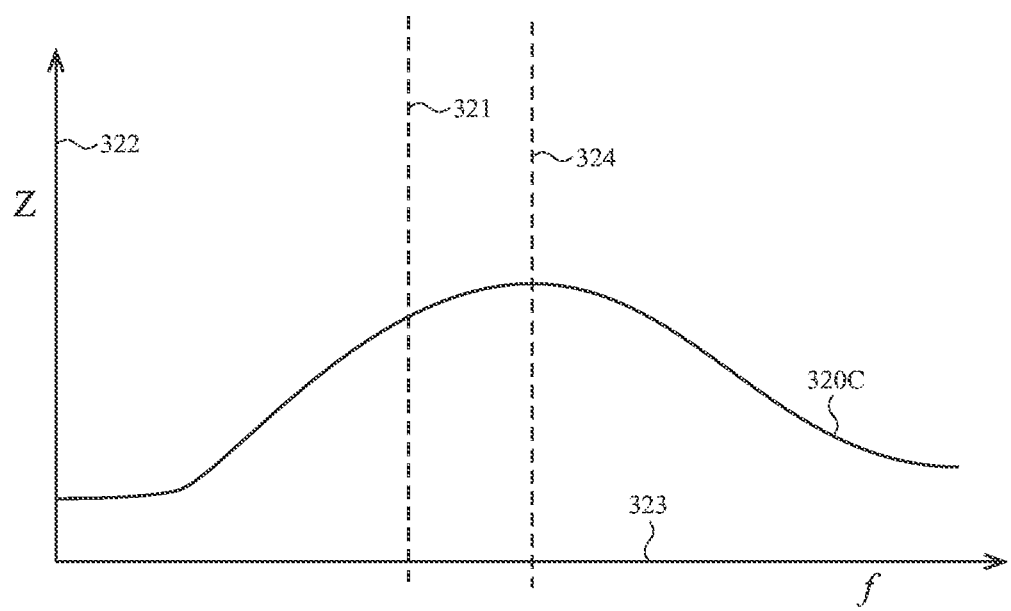
FIG. 3C depicts another example impedance curve of the acoustic transducer of FIG. 2C.

FIGS. 3A-3C depict example impedances of a voice coil subjected to different conditions. In particular, FIG. 3A depicts impedance as a function of frequency over a predetermined frequency range for a dry or normally operating acoustic module. FIG. 3B depicts impedance as a function of frequency over a range for an acoustic module having a first type of blockage, which may correspond to a foreign object (e.g., a liquid) being present on a diaphragm or membrane of the acoustic module. FIG. 3C depicts impedance as a function of frequency over a range for an acoustic module having a second type of blockage, which may correspond to an object (e.g., a finger) blocking one or more openings in the housing of the device. By analyzing the impedance over a predetermined range, the device may be configured to distinguish between the operating conditions associated with FIGS. 3A, 3B, and 3C.

FIG. 3A depicts the impedance curve 320A of an example acoustic transducer operating in dry or normal, unobstructed conditions. With reference to FIG. 2A, the acoustic transducer may include a voice coil 210, which may exhibit an impedance response in accordance with the impedance curve 320A of FIG. 3A when operating in an unobstructed state.

The highest point of the impedance curve 320A may correspond to the resonant frequency 321 of the acoustic module 205 in a dry or unobstructed condition. The impedance curve 320A may exhibit a peak or local maxima at the resonant frequency 321 because the resonant frequency 321 corresponds to the largest and possibly the most rapid displacement over the normal operating frequency range of the acoustic module 205. Large and rapid displacement tends to increase back EMF, which may be evidenced by an increase in impedance of the voice coil. In some cases, resonant frequency 321 of the acoustic module 205 under dry or unobstructed conditions may serve as a reference frequency at which an impedance is monitored. Changes in impedance measured at this reference frequency may indicate that a blockage has occurred and/or a type of blockage that is affecting the performance of the acoustic module 205.

In general, a blockage that restricts motion of the diaphragm 209 will reduce the impedance 322 at a respective frequency 323 because the movement of the diaphragm 209 will be restricted or altered (as compared to in an unobstructed condition). FIGS. 3B and 3C represent example impedance curves when an acoustic module has been obstructed.

FIG. 3B depicts the impedance curve 320B that may correspond to a first type of blockage condition in which a foreign object, such as a liquid, is present on or near the diaphragm or voice coil of the acoustic transducer. By way of illustration, this type of blockage may correspond to the example of FIG. 2B, in which the foreign object 250 (e.g., a liquid) restricts or impedes the motion of the diaphragm 209 and/or the voice coil 210. In some cases, the presence of the foreign object 250 may increase the amount of mass that is displaced during operation of the acoustic transducer in which the diaphragm 209 moves or vibrates. The additional mass may restrict the motion of the diaphragm 209 and alter the natural or resonant frequency of the acoustic transducer. In some cases, the resonant frequency of the acoustic transducer is shifted outside of the predetermined frequency range represented by the impedance curve 320B of FIG. 3B.

As shown in FIG. 3B, this type of blockage may result in an impedance curve 320B that is substantially flattened due to the presence of the foreign object 250 (e.g., a liquid). As compared to the unobstructed acoustic transducer of FIG. 3A having curve 320A, the impedance curve 320B of FIG. 3B may exhibit no substantial peak or local maxima with regard to measured impedance 322 over the frequency range 323. Notably, the impedance at the reference frequency 321 (e.g., the unobstructed resonant frequency) may be lower or reduced for the impedance curve 320B as compared to the impedance curve 320A. In some cases, the average impedance over the frequency range 323 may be lower or reduced for the impedance curve 320B as compared to the impedance curve 320A. The predetermined frequency range may, for example, correspond to the audible frequency range of the human ear. In some cases, the predetermined frequency range is between 20 and 20,000 Hz.

FIG. 3C shows the impedance curve 320C that may correspond to a second type of blockage condition in which an object, such as a finger or other body part, partially blocks or obstructs the acoustic opening in the housing of the device. By way of illustration, this type of blockage may correspond to the example of FIG. 2C, depicting an object 251 blocking the one or more of the set of acoustic openings 104. The blockage may change or shift the resonant frequency of the acoustic transducer from 321 to 324 as illustrated by the impedance curve 320C. This type of blockage condition may also distort and/or flatten the impedance curve 320C due to air pressure blocking the one or more of the set of acoustic openings 104.

FIGS. 3A-3C illustrate that the impedances 322 are different based on the type and extent of the blockage. As such, the electronic device 100 (and/or the control circuitry 213) may apply power to the voice coil 210, measure the impedance 322 at the reference or resonant frequency 321 (where the difference in impedance 322 would be the greatest if a blockage exists), and determine, based on a measured impedance or change in impedance, whether or not there is a blockage (such as liquid present in the acoustic passage). Based on the impedance 322 at the resonant frequency 321, the electronic device 100 (and/or the control circuitry 213) may determine the type of the blockage, the extent of the blockage, and/or various characteristics of the blockage.

By way of example, the electronic device 100 (and/or the control circuitry 213) may determine that the impedance 322 corresponds to the relatively flat impedance curve 320B of FIG. 3B rather than the impedance curve 320C of FIG. 3C. As such, the electronic device 100 (and/or the control circuitry 213) may determine that a foreign object is potentially contacting the diaphragm as opposed to an object merely blocking a port or opening. Determining that the type of blockage or obstruction corresponds to this type of blockage condition may be important in deciding whether or not to employ an evacuation measure or protocol.

By way of still another example, the electronic device 100 (and/or the control circuitry 213) may determine that the impedance 322 corresponds to the impedance curve 320C of FIG. 3C rather than the impedance curve 320B of FIG. 3B. As such, the electronic device 100 (and/or the control circuitry 213) may determine that one or more of the set of acoustic openings 104 may be blocked but a foreign object is not present in the acoustic passage 206. Determining that the type of blockage or obstruction corresponds to this type of blockage condition may be important in deciding to forgo or suppress an evacuation measure or protocol.

In some cases a degree of blockage, a type of foreign material or object, or an amount of foreign object ingress may be determined using an impedance measurement. In one example, the more that a port is obstructed or blocked, the lower the measured impedance and/or the greater the shift in the resonant frequency of the acoustic transducer. As such, the electronic device 100 (and/or the control circuitry 213) may estimate an amount of blockage of the port or opening. In another example, the more liquid that is present in the acoustic passage 206, the lower the measured impedance at the reference or resonant frequency 321. As such, the electronic device 100 (and/or the control circuitry 213) may estimate an amount of the liquid that is present based on the impedance 322.

Figure 4:
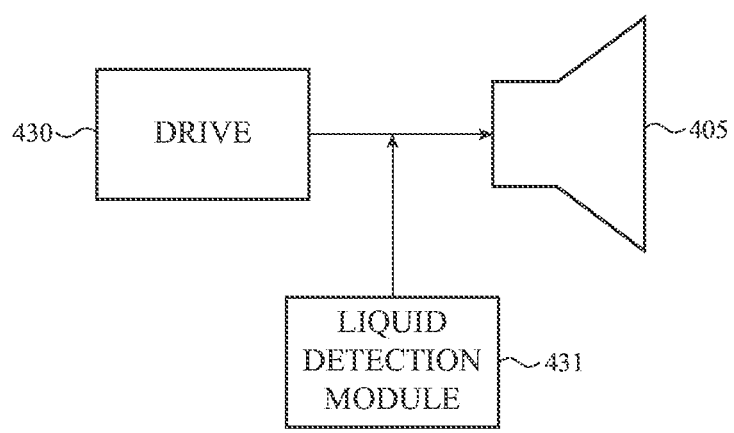
FIG. 4 is a simplified schematic embodiment of an acoustic module having a liquid detection module.

FIG. 4 is a simplified schematic of an acoustic module with a liquid detection module. In this example, the circuitry or controller includes a drive module 430 connected to an acoustic transducer 405, which may include a voice coil or other similar element. The circuitry or controller may correspond to control circuitry 213 described above with respect to FIGS. 2A-2C. The circuitry or controller may also include a liquid detection module 431, which is configured to measure the impedance or changes in impedance of the acoustic transducer 405. In some cases the liquid detection module 431 includes a high impedance sensing resistor and/or other impedance measuring device that is configured to measure small changes in impedance. In some cases the liquid detection module 431 is selectively activated to minimize any impact to performance of the acoustic module during ordinary use. In some cases, the liquid detection module 431 remains connected or activated and is configured with high-impedance elements that reduce the amount of current used by the liquid detection module 431 during ordinary use. In some cases, the liquid detection module 431 may be connected to the acoustic module 205 in parallel with the drive 430. This may allow the liquid detection module 431 to detect impedance without interfering with the acoustic transducer 405. However, it is understood that this is an example and other circuit configurations are possible and contemplated.

With reference again to FIG. 2A, the electronic device 100 (and/or the control circuitry 213) may measure and/or evaluate the impedance of the voice coil 210 using one or more measurement protocols. For example, the impedance may be measured over a regularly repeating time interval or continuously (when the acoustic module 205 is not being used to produce or receive acoustic signals). If the impedance measurement includes a measurement while the acoustic module 205 is being operated at a resonant or reference frequency, the impedance measurement may not occur simultaneously with the normal sound-producing or sound-recording operations of the acoustic module 205. In some cases, the impedance measurement is performed during or simultaneous to a sound-producing or sound-recording operation.

The impedance may also be measured upon the occurrence of a triggering condition. In some cases, one or more other sensors (e.g., the touch sensor 101 of FIG. 1) may be used to determine if a blockage condition may exist, which may be used to trigger an impedance measurement. Exposure of the electronic device 100 to liquid may be detectable by the capacitive touch screen. If the capacitive touch screen detects such a possible exposure, the electronic device 100 (and/or the control circuitry 213) may receive a signal from the capacitive touch screen and determine to measure and/or evaluate the impedance of the voice coil 210. In some implementations, the electronic device 100 (and/or the control circuitry 213) may measure and/or evaluate the impedance of the voice coil 210 prior to signaling the acoustic module 205 to produce sound waves (e.g., applying power to the voice coil 210). By way of another example, the electronic device 100 (and/or the control circuitry 213) may measure and/or evaluate the impedance of the voice coil 210 in response to receiving a user instruction to measure and/or evaluate.

Signals from various other sensors and/or other components may also be used to trigger measurement and/or evaluation. For example, the microphone may detect sound produced by the acoustic module 205 via the acoustic opening 103. The electronic device 100 (and/or the control circuitry 213) may compare the detected sound to what the acoustic module 205 had been instructed to produce. If the detected sound is other than what is expected, the electronic device 100 (and/or the control circuitry 213) may measure and/or evaluate the impedance of the voice coil 210 under the assumption that the acoustic passage 206 may be partially or fully blocked.

Measuring impedance of the voice coil 210 involves applying power to the voice coil 210. As a result, the diaphragm 209 may move and sound waves may be produced. This may be noticeable to a user, which may not always be desirable. As such, in some implementations, an ambient acoustic level or other sound level may be detected (such as using the microphone and/or another sound detector to determine a measured acoustic level) and measurement may be performed once the detected sound is above a threshold amount of sound. The threshold amount of sound may be an amount of sound below which, though not above which, the movement of the diaphragm 209 during measurement can be discerned by human hearing. In still other implementations, a user may be prompted to measure and/or evaluate and the electronic device 100 (and/or the control circuitry 213) may measure and/or evaluate upon receiving confirmation from the user.

In various implementations, the presence of liquid may detected based on a reduction of impedance over a range of frequencies that includes the resonant frequency as compared to a reference value. In such an implementation, the reference value may correspond to an operation of the voice coil 210 without the presence of liquid. The presence of liquid may be detected when the measured impedance is approximately equal to the impedance of the voice coil 210 when dry at a non-resonant frequency.

When the electronic device 100 detects a blockage, the electronic device 100 may perform one or more actions to remove the blockage which may be referred to as an evacuation measure or protocol. In some implementations, if the electronic device 100 detects that one or more of the set of acoustic openings 104 is blocked but liquid and/or other material or foreign contaminants (such as dirt, oil, and so on) is not in the acoustic passage 206, the electronic device 100 may provide a notification to a user to clear the set of the acoustic openings 104.

In various implementations, if the electronic device 100 determines that liquid and/or other material or foreign contaminants (such as dirt, oil, and so on) is present, the electronic device 100 may perform one or more actions to drive out, purge, and/or otherwise remove the liquid from the acoustic passage 206. For example, the electronic device 100 may provide a notification to a user to remove the liquid. By way of another example, the electronic device 100 may activate a heating element that evaporates the liquid.

In various examples, the electronic device 100 may apply voltage to the voice coil 210 in order to vibrate and/or otherwise move the diaphragm 209. Movement of the diaphragm 209 may drive the liquid from the acoustic passage 206. In some situations, moving the diaphragm 209 to drive out liquid may be noticeable to a user, and may be undesirable. In some implementations, the electronic device 100 may apply the voltage such that sound waves produced are outside the range perceptible to human hearing (approximately 20 Hz-20 kHz). As such, the user would not notice driving out the liquid. In other implementations, the electronic device 100 may first prompt the user that driving out the liquid may be performed and perform driving out the liquid once the user confirms. In still other implementations, the electronic device 100 may use a sound detector such as the microphone to detect an ambient or other sound level and may drive out the liquid once sound is exceeding a threshold amount where the threshold amount would obscure the sound from driving out the liquid.

In various implementations, various frequencies may be used to drive out the liquid. In some cases, a sweep may be performed through a range of frequencies. The impedance may be monitored and driving out the liquid may be continued until the impedance (and/or monitoring of sound using the microphone or other sound detector) indicates that the liquid is gone, the sweep continuing through the range of frequencies as long as the impedance indicates the liquid is still present. In other cases, tones of one or more frequencies (such as tones previously found successful in removing liquid from the acoustic passage, which the control circuitry 213 may store in one or more non-transitory storage media) may be played until the impedance (and/or monitoring of sound using the microphone or other sound detector) indicates the liquid is gone, the frequencies and/or other properties varied as long as the liquid is still present.

In some implementations, a broadband or noise signal may be produced rather than a tone at a particular frequency or frequencies. In some cases, noise may be characterized as a broadband signal that includes multiple or a range of frequencies. Users are less likely to perceive a noise-type output as compared to a tone having a particular frequency or frequencies. As such, voltage applied to the acoustic transducer to use noise to drive out the liquid may be less noticeable to users even though produced at a volume level that may be otherwise perceptible.

Additionally, the electronic device may determine whether or not the electronic device has ever been exposed to a particular contaminant. For example, many warranties may be voided if a device has ever been immersed in and/or significantly exposed to water. As such, the electronic device may perform various actions upon detecting liquid in the acoustic passage 206.

For example, the electronic device may be operable to respond to a query as to whether the electronic device has been exposed to contaminants such as water. Upon detecting liquid in the acoustic passage (e.g., acoustic passage 206 of FIGS. 2A-2C), the electronic device may utilize a communication component to notify a computing device (such as one maintained by or for a warrantee provider, manufacturer, retailer, and/or other entity) regarding the detection. Alternatively, the electronic device may store information regarding the detection in a non-transitory storage media and may provide such information when requested via the communication component, by a user, and the like.

Figure 5:
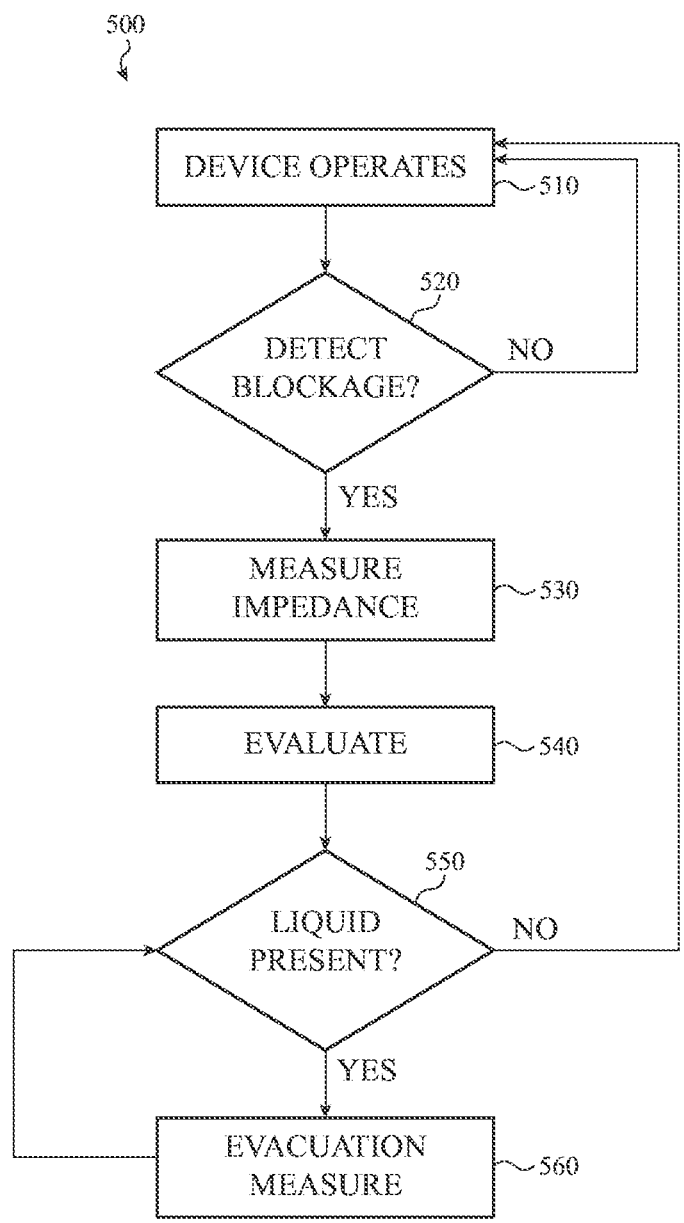
FIG. 5 depicts a flow chart illustrating a first example method for detecting liquid in an acoustic module using impedance and removing the liquid. The method may be performed by the electronic devices of FIGS. 1, 2A-2C, and/or 4.

FIG. 5 depicts a flow chart illustrating a first example method 500 for detecting liquid in an acoustic module using impedance and removing the liquid. The method 500 may be performed by the electronic devices or hardware configurations of FIGS. 1, 2A-2C, and/or 4.

At 510, a device operates. For example, the device may be powered on and perform normal operations in accordance with a standard protocol or normal use. The flow proceeds to 520 where the device determines whether or not to detect a blockage. If not, the flow returns to 510 where the device continues to operate. Otherwise, the flow proceeds to 530.

At 530, the device measures the impedance of the acoustic transducer (e.g. a transducer having a voice coil). The flow then proceeds to 540 where the device evaluates the impedance of the acoustic transducer. The impedance of the acoustic transducer may be measured in one or more of the following ways. In one example, the impedance is measured at a reference frequency, which may correspond to the resonant or natural frequency of the acoustic transducer in a dry or unobstructed condition. Additionally or alternatively, an average, weighted average, or other composite impedance measurement may be computed over a predetermined frequency range. In some cases, a change in impedance over a predetermined time interval is measured. Various other techniques may be used to evaluate the impedance or a change in impedance against various values that correspond to different conditions, compare the impedance against an expected impedance, or otherwise characterize the impedance response of the acoustic transducer.

The flow then proceeds to 550 where the device determines if there is blockage based on the measured impedance. In particular, the device may determine if there is liquid or another foreign object present in a passage or on the diaphragm of the acoustic transducer based on the measured impedance. If it is determined that there is no blockage, the flow returns to 510 where the device continues to operate. Otherwise, the flow proceeds to 560.

With regard to 550, a blockage may be determined based on one or more of the following techniques for evaluating or analyzing the impedance. For example, a blockage condition may be detected if the peak impedance is reduce or lowered. A blockage condition may also be detected if the peak impedance is shifted or moved with respect to a reference frequency (e.g., the resonant frequency of an unimpeded speaker). In general, any aspect of an impedance response or curve for a given frequency or over a range of frequencies may be used to make the determination in accordance with operation 550. Example analysis of the impedance or impedance response of a device are also described above with respect to FIGS. 3A-3C.

At 560, the device (and/or circuitry of the device) may employ an evacuation measure or protocol that attempts to drive out, purge, and/or otherwise remove the liquid. Attempting to drive out the liquid may include applying a drive signal, voltage signal, or drive voltage to the acoustic transducer to move the attached diaphragm. In some cases, an updated impedance measurement is taken while applying the drive signal. Based on the updated impedance measurement, the drive signal may be adjusted or stopped. The flow then returns to 550 where it is determined whether or not the liquid is still present.

Although the example method 500 is illustrated and described as including particular operations performed in a particular order, it is understood that this is an example. In various implementations, various orders of the same, similar, and/or different operations may be performed without departing from the scope of the present disclosure.

For example, the method 500 is illustrated and described as the device determining whether or not the liquid is still present after attempting to drive out the liquid. However, in various implementations, the device may return to 510 and continue to operate after attempting to drive out the liquid without determining whether the liquid is still present or not.

Figure 6:
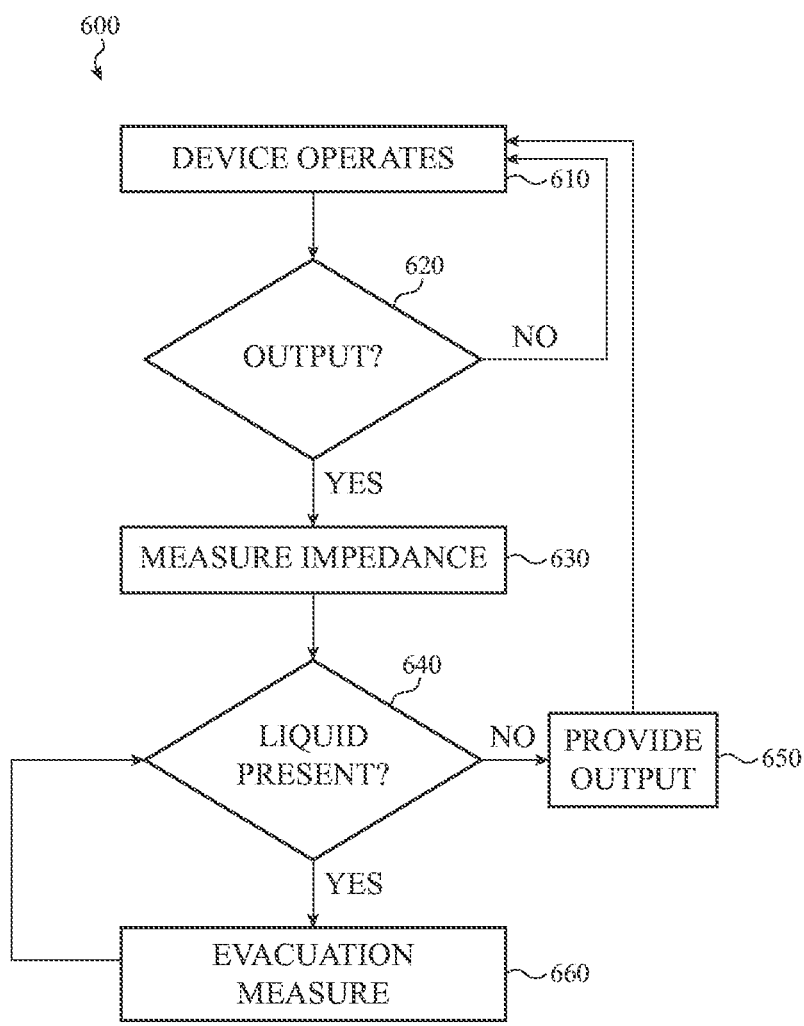
FIG. 6 depicts a flow chart illustrating a second example method for detecting liquid in an acoustic module using impedance and removing the liquid. The method may be performed by the electronic devices of FIGS. 1, 2A-2C, and/or 4.

FIG. 6 depicts a flow chart illustrating a second example method 600 for detecting liquid in an acoustic module using impedance and removing the liquid. The method 600 may be performed by the electronic devices or hardware of FIGS. 1, 2A-2C, and/or 4.

At 610, a device operates. The flow proceeds to 620 where the device determines whether or not to provide output using an acoustic module such as a speaker. For example, the output may include providing a notification, playing sound, and so on. If not, the flow returns to 610 where the device continues to operate. Otherwise, the flow proceeds to 630.

At 630, the device measures the impedance of an acoustic transducer of an acoustic module. The flow then proceeds to 640 where the device determines based on the impedance whether or not liquid is present in an acoustic passage or port associated with the acoustic module. If not, the flow proceeds to 650 where the device provides the output using the acoustic module before the flow returns to 610 and the device continues to operate. Otherwise, the flow proceeds to 660.

At 660, the device performs an evacuation measure or protocol that is configured to drive out, purge, and/or otherwise remove the liquid. The flow then returns to 640 where it is determined whether or not the liquid is still present.

Although the example method 600 is illustrated and described as including particular operations performed in a particular order, it is understood that this is an example. In various implementations, various orders of the same, similar, and/or different operations may be performed without departing from the scope of the present disclosure.

For example, the method 600 is illustrated and described as the device determining whether or not liquid is present in the acoustic passage. However, in various implementations, the device may determine whether or not various contaminants or materials are present as opposed to liquid.

Figure 7:
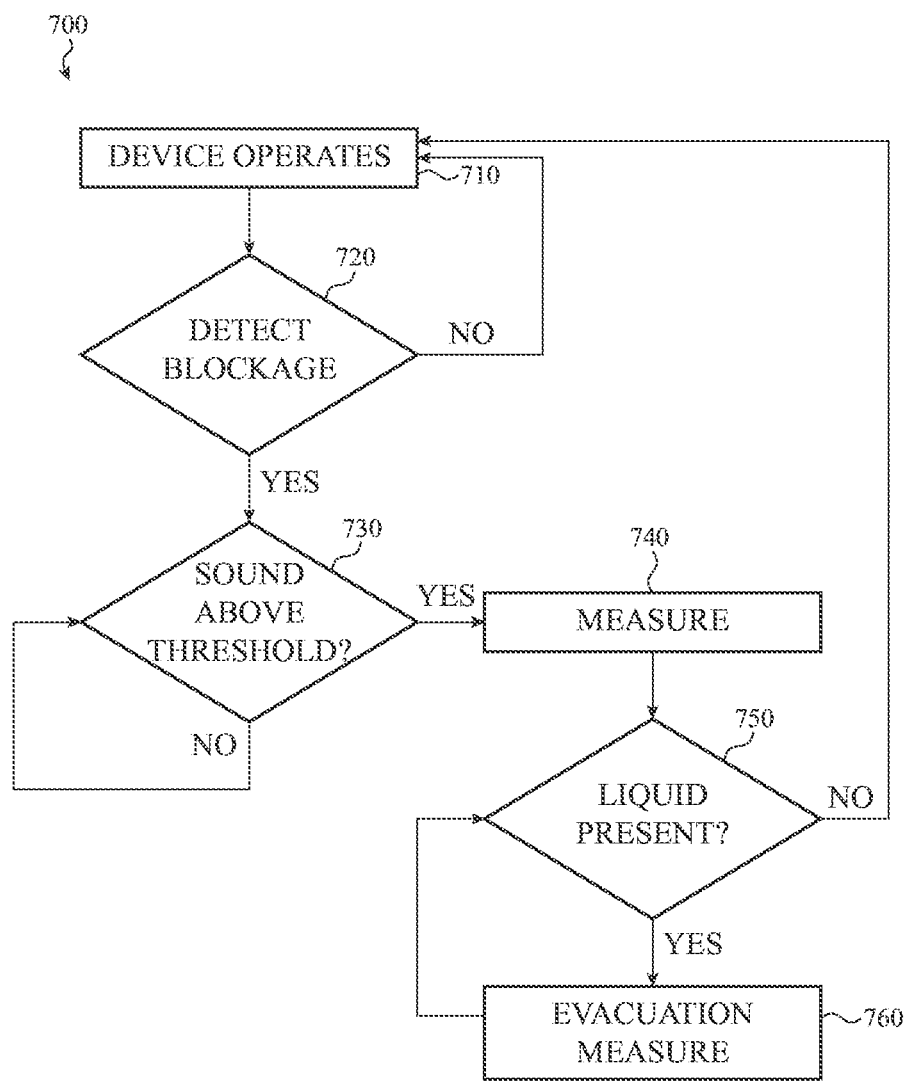
FIG. 7 depicts a flow chart illustrating a third example method for detecting liquid in an acoustic module using impedance and removing the liquid. The method may be performed by the electronic devices of FIGS. 1, 2A-2C, and/or 4.

FIG. 7 depicts a flow chart illustrating a third example method 700 for detecting liquid in an acoustic module using impedance and removing the liquid. The method 700 may be performed by the electronic devices of FIGS. 1, 2A-2C, and/or 4.

At 710, a device operates. The flow proceeds to 720 where the device determines whether or not to measure the impedance of an acoustic transducer of an acoustic module. If not, the flow returns to 710 and the device continues to operate. Otherwise, the flow proceeds to 730.

At 730, the device determines whether or not ambient or other detected sound is above a threshold amount. The threshold amount may be an amount that would obscure or otherwise cover sound produced by measuring impedance of the acoustic transducer. If not, the flow returns to 730 where the threshold is again evaluated. Essentially, the device may wait until the threshold amount of sound is detected. Otherwise, the flow proceeds to 740.

At 740, the device measures the impedance of the acoustic transducer of the acoustic module. The flow then proceeds to 750 where the device determines based on the impedance whether or not liquid is present in an acoustic passage or port associated with the acoustic module. If not, the flow returns to 710 and the device continues to operate. Otherwise, the flow proceeds to 760.

At 760, the device employs an evacuation measure or protocol that is configured to drive out, purge, and/or otherwise remove the liquid. The flow then returns to 750 where it is determined whether or not the liquid is still present (such as using the impedance, monitoring sound waves produced by the diaphragm using one or more microphones, and so on).

Although the example method 700 is illustrated and described as including particular operations performed in a particular order, it is understood that this is an example. In various implementations, various orders of the same, similar, and/or different operations may be performed without departing from the scope of the present disclosure.

For example, the method 700 is illustrated as the device waiting until the detected sound meets the threshold amount. However, in various implementations, the device may continue to wait for a period of time before returning directly to 710 without measuring impedance. In other implementations, the device may wait for the period of time and then measure impedance regardless of sound levels.

Figure 8:
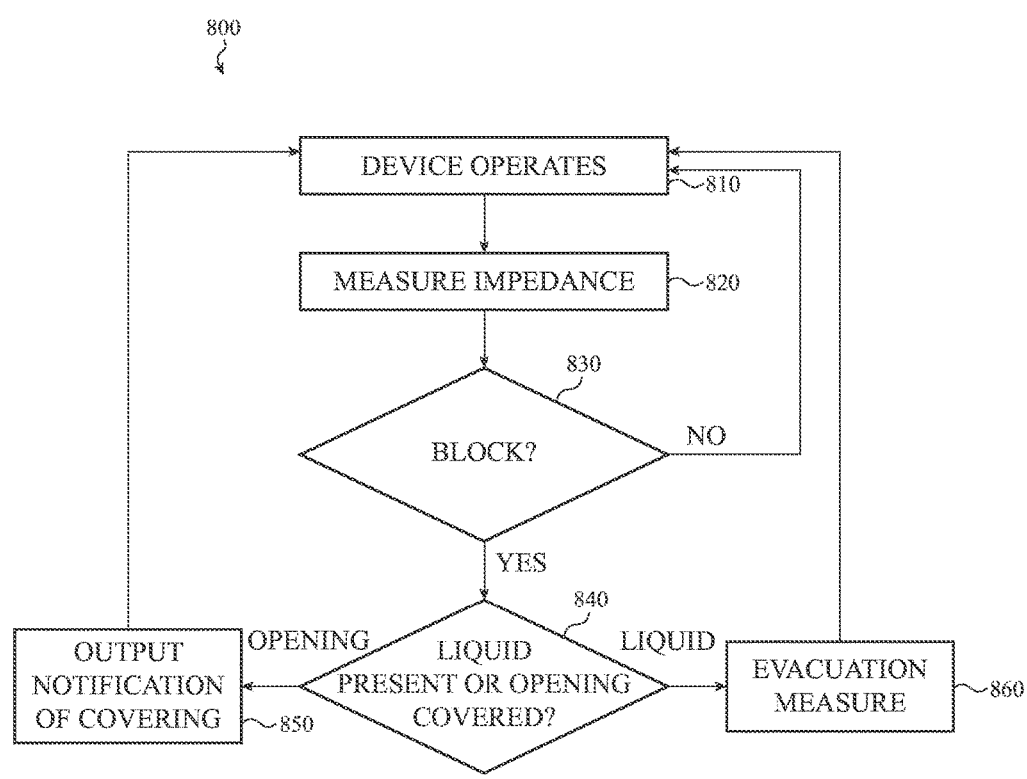
FIG. 8 depicts a flow chart illustrating an example method for detecting a blockage in an acoustic module using impedance and removing the blockage. The method may be performed by the electronic devices of FIGS. 1, 2A-2C, and/or 4.

FIG. 8 depicts a flow chart illustrating an example method 800 for detecting a blockage in an acoustic module using impedance and removing the blockage. The method 800 may be performed by the electronic devices or hardware of FIGS. 1, 2A-2C, and/or 4.

At 810, a device operates. The flow proceeds to 820 where the device measures the impedance of an acoustic transducer of an acoustic module. The flow then proceeds to 830 where the device determines based on the impedance whether or not an acoustic passage or port associated with the acoustic module is blocked. If not, the flow returns to 810 and the device continues to operate. Otherwise, the flow proceeds to 840.

At 840, the device determines based on the impedance whether the block is caused by liquid or other material in the acoustic passage or whether an opening connecting the acoustic passage to an external environment is covered. If the opening is covered, the flow proceeds to 850. Otherwise, the flow proceeds to 860.

At 850, after the device determines the opening is covered, the device outputs a notification to a user that the opening is covered. The flow then returns to 810 where the device continues to operate.

At 860, after the device determines that liquid or other material is present, the device employs an evacuation measure or protocol that is configured to drive out, purge, and/or otherwise remove the liquid. The flow then returns to 810 where the device continues to operate.

Although the example method 800 is illustrated and described as including particular operations performed in a particular order, it is understood that this is an example. In various implementations, various orders of the same, similar, and/or different operations may be performed without departing from the scope of the present disclosure.

For example, the method 800 is illustrated and described as providing a notification to the user if the opening is covered, but not if liquid is present in the acoustic passage. However, in various implementations, the device may output a message to a user that liquid is present and then drive out the liquid upon receiving a confirmation from the user.

Figure 9:
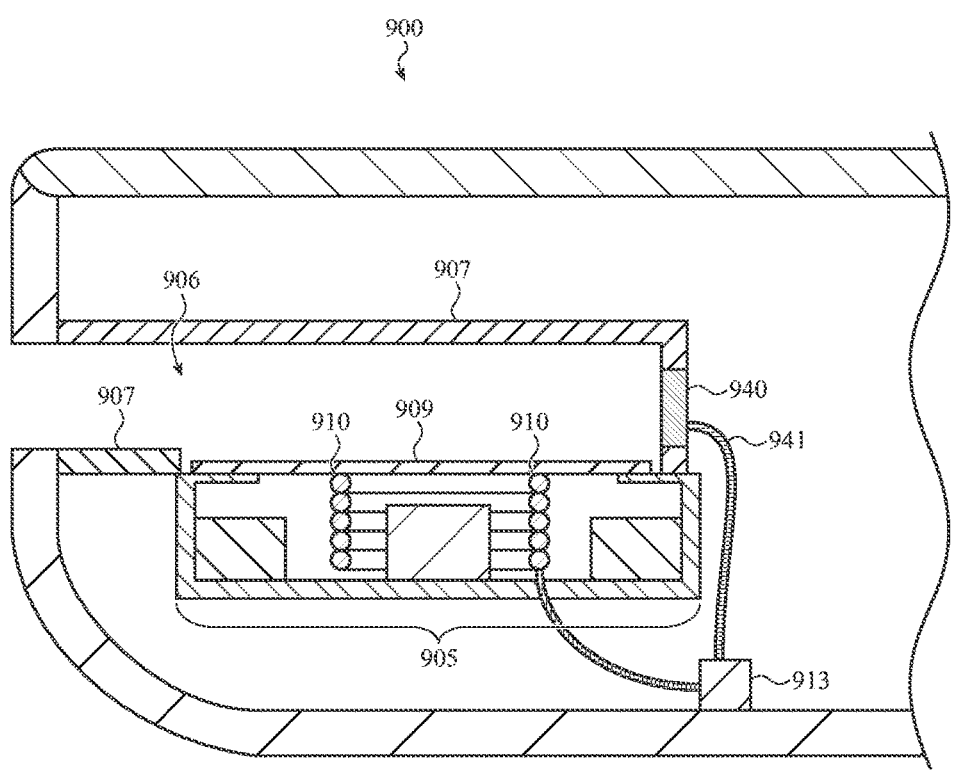
FIG. 9 depicts an alternative example of the electronic device of FIG. 2A.

FIG. 9 depicts an alternative example of the electronic device 100 of FIG. 2A. As contrasted with the electronic device 100 of FIG. 2A, the electronic device 900 and/or the circuitry 913 may not move the diaphragm 909 using the acoustic transducer 910. Instead, a transducer 940 may be signaled by the circuitry 913 via an electrical conduit 941 to evacuate or drive out the liquid. The transducer 940 may be disposed on the structure 907.

The transducer 940 may be any kind of component operable to generate motion to drive out the liquid from the acoustic passage 906. For example, the transducer 940 may include a diaphragm that can be vibrated and/or otherwise moved to drive out the liquid. The transducer 940 may vibrate such a diaphragm so as to not produce sound waves perceptible to a human. By way of another example, the transducer 940 may include piezoelectric material operable to deflect, deform, and/or otherwise move to drive out the liquid. In still another example, the transducer 940 may include a flap or other mechanism that is moveable to drive out the liquid. Various transducer 940 configurations are possible and contemplated.

As described above and illustrated in the accompanying figures, the present disclosure relates to detection of liquid in an acoustic module, such as a speaker or microphone, using impedance and/or removal of the liquid. The acoustic module includes an acoustic transducer coupled to a diaphragm. The diaphragm faces an acoustic passage through which sound waves produced or received by the diaphragm travel. Blockages in the acoustic passage (such as liquid in the passage contacting the diaphragm, a finger covering an acoustic opening connecting the acoustic passage to an external environment, and so on) alter the impedance of the acoustic transducer. By measuring and evaluating the impedance, the acoustic module and/or an associated electronic device determines whether or not a blockage is present.

In the present disclosure, the methods disclosed may be implemented as sets of instructions or software readable by a device. Further, it is understood that the specific order or hierarchy of steps in the methods disclosed are examples of sample approaches. In other embodiments, the specific order or hierarchy of steps in the method can be rearranged while remaining within the disclosed subject matter. The accompanying method claims present elements of the various steps in a sample order, and are not necessarily meant to be limited to the specific order or hierarchy presented.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. An electronic device, comprising:
a housing;
an acoustic passage internal to the housing;
an acoustic transducer coupled to the acoustic passage; and
circuitry electrically coupled to the acoustic transducer and operable to:
measure an impedance of the acoustic transducer at approximately a reference frequency of the acoustic transducer; and
detect a presence of liquid based on the measured impedance; wherein:
the reference frequency corresponds to a resonant frequency of the acoustic transducer in an unobstructed condition; and
the presence of liquid is detected based on a reduction of impedance over a range of frequencies that includes the resonant frequency as compared to a reference value.

2. The electronic device of claim 1, wherein
the reference value corresponds to an operation of the acoustic transducer without the presence of liquid.

3. The electronic device of claim 2, wherein:
the presence of liquid is detected when the measured impedance is approximately equal to the impedance of the acoustic transducer when dry at a non-resonant frequency.

4. An electronic device, comprising:
a housing;
an acoustic passage internal to the housing;
an acoustic transducer coupled to the acoustic passage; and
circuitry electrically coupled to the acoustic transducer and operable to:
measure an impedance of the acoustic transducer at approximately a reference frequency of the acoustic transducer;
detect a presence of liquid based on the measured impedance; and
apply a drive signal to a transducer, the drive signal is configured to purge the liquid from the acoustic passage.

5. The electronic device of claim 4, wherein:
the transducer is the acoustic transducer; and
the drive signal is a voltage signal.

6. The electronic device of claim 4, wherein the transducer is separate from the acoustic transducer.

7. The electronic device of claim 4, wherein the circuitry is further operable to:
measure an updated impedance of the acoustic transducer while applying the drive signal; and
adjust the drive signal based on the updated impedance.

8. An electronic device, comprising:
a housing;
a port defined in the housing;
an acoustic module coupled to the port, the acoustic module including an acoustic transducer; and
a controller coupled to the acoustic module and operable to:
measure an impedance of the acoustic transducer at approximately a resonant frequency of the acoustic transducer;
determine a blockage condition based on the measured impedance; and
distinguish if the blockage condition is due to a blockage of the port or a foreign material within the housing.

9. The electronic device of claim 8, wherein the controller is further configured to estimate a type of foreign material within the housing based on the measured impedance.

10. The electronic device of claim 8, wherein the controller measures the impedance prior to signaling the acoustic module to provide output.

11. The electronic device of claim 8, wherein the acoustic module comprises at least one of a speaker or a microphone.

12. An electronic device, comprising:
a housing;
a port defined in the housing;
an acoustic module coupled to the port, the acoustic module including an acoustic transducer;
a microphone; and
a controller coupled to the acoustic module and the microphone, the controller operable to:
measure an impedance of the acoustic transducer at approximately a resonant frequency of the acoustic transducer;
determine a blockage condition based on the measured impedance;
measure an ambient acoustic level; and
in response to the measured ambient acoustic level exceeding a threshold, drive the acoustic transducer at the resonant frequency and measure the impedance of the acoustic transducer.

13. The electronic device of claim 12, wherein the controller:
determines the blockage condition is a presence of liquid in the port; and
drives the liquid out of the port.

14. The electronic device of claim 13, wherein the controller ceases driving the liquid out of the port in response to an updated impedance.

15. The electronic device of claim 14, wherein the updated impedance indicates the liquid is not present in the port.

16. An electronic device, comprising:
   an enclosure;
   an acoustic module including an acoustic transducer, the acoustic module coupled to a passage within an interior of the enclosure;
   a detector coupled to the acoustic transducer operable to measure a change in impedance of the acoustic transducer; and
   a processing unit coupled to the detector operable to determine a blockage condition based on the change in impedance; wherein the processing unit uses the impedance to determine at least one of an amount of a contaminant or a type of a contaminant.

17. The electronic device of claim 16, wherein the detector comprises a sensing resistor.

18. The electronic device of claim 16, further comprising a capacitive touch component coupled to the processing unit, wherein the detector measures the impedance in response to a signal from the capacitive touch component.

19. The electronic device of claim 16, wherein the processing unit is operable to respond to a query regarding whether the electronic device has been exposed to contaminants.

20. The electronic device of claim 16, wherein the processing unit is operable to prompt a user before attempting to remove contaminants from the passage.

* * * * *